United States Patent [19]
Zheng et al.

[11] Patent Number: 6,093,436
[45] Date of Patent: Jul. 25, 2000

[54] BEVERAGE ANTIOXIDANT SYSTEM

[75] Inventors: Ying Zheng, Dublin, Ohio; Xiaoping Fu, Epalinges, Switzerland; Tawfik Yousef Sharkasi, Dublin, Ohio

[73] Assignee: Nestec S.A., Vevey, Switzerland

[21] Appl. No.: 09/018,566

[22] Filed: Feb. 4, 1998

[51] Int. Cl.⁷ .................................. A23B 1/27; A23F 5/00
[52] U.S. Cl. ........................ 426/541; 426/590; 426/594; 426/595
[58] Field of Search .................................... 426/541, 590, 426/594, 595

[56] References Cited

U.S. PATENT DOCUMENTS

| | | | |
|---|---|---|---|
| 4,957,749 | 9/1990 | Prieels et al. | 426/10 |
| 5,384,143 | 1/1995 | Koyama et al. | 426/546 |

FOREIGN PATENT DOCUMENTS

| | | |
|---|---|---|
| 0 207 039 | 8/1989 | European Pat. Off. . |
| 0 442 781 | 8/1991 | European Pat. Off. . |
| 6-141776 | 5/1994 | Japan . |

OTHER PUBLICATIONS

Database Abstract (Dialog) for Mutation Research, (4). pp. 383–392. Authors: Suwa et al, 1982.

Database Abstract (Dialog) for Food Science and Technology, 34 (3). pp. 195–199. Authors: Ramteke et al, 1997.

Solehah et al., "Enzymes for Improved Extraction and Stabilization of Colour and Flavour of Orange Juice", *J. Food Sci. Technol.,* (1994) vol. 31, No. 6, pp. 508–510.

*Primary Examiner*—Anthony J. Weier
*Attorney, Agent, or Firm*—Pennie & Edmonds LLP

[57] ABSTRACT

An antioxidant system for beverages, particularly coffee beverages. The antioxidant system is made up of glucose oxidase, a glucose oxidase substrate and an inorganic oxygen scavenger. The beverages have improved aroma and flavor.

15 Claims, No Drawings

BEVERAGE ANTIOXIDANT SYSTEM

FIELD OF THE INVENTION

This invention relates to an antioxidant system for beverages; especially beverages in ready-to-drink form. The invention also relates to beverages and beverage precursors which contain the antioxidant system and to processes for removing oxygen using the antioxidant system.

BACKGROUND OF THE INVENTION

Many beverages suffer adverse effects from exposure to oxygen. This is particularly the case with ready-to-drink beverages; especially ready-to-drink coffee beverages. Ready-to-drink coffee beverages are produced by extracting soluble coffee solids from roasted and ground coffee beans using hot water. The extract obtained may then be diluted to a desired concentration, usually to contain about 1% by weight of soluble coffee solids. Various additives are added to the diluted extract which is then filled into containers. The containers are then sealed and subjected to retorting. Certain intermediate steps may also be carried out. For example, the extract may be concentrated and dried to powder prior to formation of the dilute extract. This is usually done when the coffee is filled into the containers at a site different than the site at which the extraction is carried out.

During this process, the coffee may be exposed to oxygen several times. For example, oxygen may be present in the hot water which is used to extract the soluble coffee solids from the roasted and ground coffee beans. Also, the coffee may be exposed to oxygen during extraction or subsequent processing such as concentration and drying. Further, oxygen may get into the container during filling. No matter where in the process the coffee is exposed to oxygen, it is now recognized that the oxygen adversely effects the flavor and aroma of the coffee beverage. In particular, the beverage loses its fresh, clean flavor and aroma; the flavor and aroma which characterizes freshly brewed coffee. Often, bitter, acid flavors develop.

Various measures have been taken in the past to reduce the influence of oxygen. Usually these methods have centered on preventing ingress of oxygen. For example, Japanese patent application 6-141776 discloses extracting coffee grounds using deoxygenated water in an inert gas atmosphere. Further, all subsequent steps, including filling of the dilute extract into containers, is done under inert gas atmosphere. The patent application describes the resulting product to have a good, fresh flavor. The inert gas recommended is nitrogen. The primary problem with this technique is its cost. Carrying out an entire extraction and filling process in a nitrogen gas atmosphere is extremely expensive. Also, deoxygenating water is not a perfect process and not all oxygen is removed.

Another approach which has been attempted is to use antioxidants during the process. For example, U.S. Pat. No. 5,384,143 describes a process in which the coffee extract is rapidly cooled to below 20° C. and then an antioxidant selected from erythorbic acid, ascorbic acid, and their water soluble salts, is added to the cooled extract. The extract is then filled into cans under oxygen free conditions. This technique is less expensive than carrying out the entire process under inert gas atmosphere but there are problems. In particular, coffee is a potent antioxidant which is able to scavenge oxygen faster than most antioxidants commonly used in foods. Therefore, although the antioxidants described in this patent remove some of the oxygen, they are not potent enough to prevent the coffee from scavenging a large portion of the oxygen present. Consequently, the coffee undergoes some oxidative damage.

A further approach has been the use of enzyme systems. For example, the use of systems based upon glucose oxidase and alcohol oxidase have been suggested. However these systems have not proved to be adequate since degradation due to oxygen still occurs. Also, these enzyme systems often produce hydrogen peroxide which is undesirable.

Therefore it is an object of this invention to provide an antioxidant system which is relatively inexpensive and which is sufficiently potent to remove oxygen from beverage components which are themselves antioxidants.

SUMMARY OF THE INVENTION

Accordingly, in one aspect, this invention provides an antioxidant system, the system comprising glucose oxidase, a glucose oxidase substrate and an inorganic oxygen scavenger.

It has been surprisingly found that the combination glucose oxidase, a glucose oxidase substrate and an inorganic oxygen scavenger is a sufficiently potent antioxidant such that small amounts are able to adequately compete with beverage components which are potent antioxidants, such as coffee. Since small amounts are required, the system therefore offers the advantage of being an inexpensive and effective antioxidant. Also, the system is food grade; especially at the small amounts required.

Preferably the glucose oxidase forms part of an enzyme mixture which includes catalase.

In another aspect, this invention provides a ready-to-drink beverage which includes an antioxidant system, the system comprising glucose oxidase, a glucose oxidase substrate and an inorganic oxygen scavenger.

The ready-to-drink beverage is preferably a coffee beverage; especially a black coffee beverage.

In a yet further aspect, this invention provides a beverage concentrate which includes an antioxidant system, the system comprising glucose oxidase, a glucose oxidase substrate and an inorganic oxygen scavenger.

The inorganic oxygen scavenger is preferably a sulfite; for example sodium sulfite.

In another aspect, this invention provides a process for reducing oxygen in a beverage, the process comprising:

adding an antioxidant system comprising glucose oxidase, a glucose oxidase substrate and an inorganic oxygen scavenger to the beverage;

filling the beverage into containers; and sealing the containers.

In another aspect, this invention provides a process for reducing oxygen in a beverage containing extracted solids, the process comprising:

adding an antioxidant system comprising glucose oxidase, a glucose oxidase substrate and an inorganic oxygen scavenger to an extraction liquid;

extracting solids from an extraction substrate using the extraction liquid to provide a beverage;

filling the beverage into containers; and sealing the containers.

Preferably, the beverage is filled into containers under oxygen reduced or oxygen free conditions. Further, further amounts of the antioxidant system may be added to the beverage prior to sealing of the containers.

DETAILED DESCRIPTION OF THE PREFERRED EMBODIMENTS

Embodiments of the invention are now described, by way of example only. This invention provides an antioxidant system which is useful for removing oxygen from beverages and beverage concentrates. The antioxidant system may be used, for example, during the processing of the beverage, in a pre-cursor to the beverage such as a beverage concentrate, or in ready-to-drink beverages. The antioxidant system is particularly suitable for use in connection with ready-to-drink, coffee beverages and will be described primarily in this context. It is to be appreciated however that this is done for simplicity of description and the antioxidant system is not limited to this application.

The antioxidant system includes a glucose oxidase (EC 1.1.3.4). The glucose oxidase catalyzes the oxidation of glucose to gluconic acid according to the following reaction scheme:

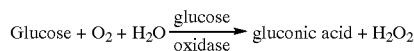

$$\text{Glucose} + O_2 + H_2O \xrightarrow{\text{glucose oxidase}} \text{gluconic acid} + H_2O_2$$

The antioxidant system may also include a catalase (EC 1.11.1.6). Then, the catalase degrades the peroxide according to the following reaction scheme:

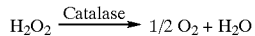

$$H_2O_2 \xrightarrow{\text{Catalase}} 1/2\, O_2 + H_2O$$

The glucose oxidase and the catalase are preferably provided in the form of an enzyme mixture. A suitable enzyme mixture is the Novozym® 358 enzyme preparation commercialized by Novo Nordisk AS of Novo Allé, 2880 Bagsvaerd, Denmark. This enzyme preparation is prepared from *Aspergillus niger* and is generally recognized as safe.

The antioxidant system also includes a glucose oxidase substrate. This takes the form of glucose. The glucose oxidase substrate may be an inherent part of the beverage itself, may be added to the beverage, or both. In the case of coffee beverages, the glucose oxidase substrate is ordinarily added to the beverage mix because coffee contains little or no glucose. However, for other beverages which inherently contain glucose, further glucose need not be added.

The antioxidant system further includes an inorganic oxygen scavenger. Sulfites are particularly useful an inorganic oxygen scavengers. Suitable sulfites include sulfur dioxide, sodium sulfite, sodium metabisulfite, anhydrous sodium bisulfite, potassium metabisulfite, anhydrous potassium bisulfite, and mixtures of these agents. Sodium sulfite is particularly preferred. Apart from further removing oxygen, the inorganic oxygen scavenger removes hydrogen peroxide generated by the glucose oxidase.

The amount of the antioxidant system used will depend upon the substance to be treated and the level of oxygen present. Also, the amounts used of the various components in the antioxidant system will depend upon the substance to be treated and the level of oxygen present. Further, the amount of enzyme used will depend upon the activity of the enzyme. These amounts will be readily determined for each situation.

However, in general, the amount of glucose oxidase used is less than about 0.5% by weight of the total weight of the substance to be treated. For example. the amount of glucose oxidase used is preferably in the range of about 0.001% to about 0.1% by weight of the total weight of the substance to be treated. An amount in the range of about 0.005% to about 0.05% by weight is especially preferred for coffee beverages. The activity of the glucose oxidase is preferably about 1500 units/ml to about 2500 units/ml; for example about 2000 units/ml. A unit is the amount of enzyme which, at a temperature of 25° C. and a pH of 5.1, catalyzes the formation of 1 μmol of $H_2O_2$.

The amount of glucose oxidase substrate which is used is conveniently less than about 1% by weight of the total weight of the substance to be treated. For example, the amount of glucose oxidase substrate used is preferably in the range of about 0.005% to about 0.5% by weight of the total weight of the substance to be treated. An amount in the range of about 0.01% to about 0.3% by weight is especially preferred for coffee beverages; for example about 0.05% by weight. The glucose oxidase substrate may be present in the substance to be treated or may be added to the substance, or both. Usually, for coffee beverages, the glucose oxidase substrate is added. For beverages which must undergo heat treatment, the amount of glucose oxidase substrate used is preferably kept to the minimum necessary to obtain the required glucose oxidase activity. In this way, the formation of undesirable Maillard reactions may be avoided.

The amount of the inorganic oxygen scavenger which is used is conveniently less than about 0.1% by weight of the total weight of the substance to be treated. For example, the amount of inorganic oxygen scavenger used is preferably in the range of about 0.001% to about 0.05% by weight of the total weight of the substance to be treated. An amount in the range of about 0.002% to about 0.03% by weight is especially preferred for coffee beverages; for example about 0.005% by weight. Further, relevant regulatory requirements concerning the maximum residual levels of inorganic oxygen scavengers in foodstuffs should be respected.

If a catalase is used, the amount used is not critical. Usually the catalase will be provided in a mixture with the glucose oxidase and hence the catalase levels will be determined by the amount of glucose oxidase used.

The antioxidant system may be used at various points during the processing of a beverage. For example, for coffee and tea beverages, the antioxidant system may be added to the water which is to be used to extract soluble solids from the coffee or tea. In this way, the water which is used for extraction may be efficiently deoxygenated. However, because the glucose oxidase denatures at temperatures above about 60° C., the treatment should be carried out prior to heating the extraction water.

The antioxidant system may also be added to the extract obtained after extraction. At the time of addition of the enzyme of the antioxidant system, the temperature of the extract should be below about 60° C. After the extract has been deoxygenated, the extract may be thermally treated; for example during concentration or drying or both. The inorganic oxygen scavenger continues to operate at temperatures above 60° C. Of course, for best effect, all further processing of the extract should be carried out under oxygen reduced or oxygen free conditions. The various techniques described in the art may be used. In this way, a beverage, beverage concentrate or beverage powder which contains the antioxidant system and low levels of oxygen may be obtained.

The antioxidant system may also be added to the beverage prior to filling of the beverage into containers. At the time of addition of the enzyme of the antioxidant system, the temperature of the beverage should be below about 60° C. After the beverage has been deoxygenated, the beverage may be retorted in the usual manner. For best effect, the subsequent filling of the beverage into containers may be carried out under oxygen reduced or oxygen free conditions. The various techniques described in the art may be used. The beverage obtained preferably contains less than about 1 ppm of dissolved oxygen; more preferably less than about 0.5 ppm dissolved oxygen.

The antioxidant system may be used in combination with any type of beverage such as tea beverages, coffee beverages, chocolate beverages, malted beverages, and the like. However the system is particularly suited for use in coffee beverages since the system is able to compete with the potent antioxidant effects of coffee. Black coffee beverages, which are intended to have a clean, fresh flavor and aroma, are especially suitable. These beverages ordinarily contain about 0.5% to about 1.5% by weight of soluble coffee solids. They may also contain a sweetener.

Specific examples are now described to further illustrate the invention.

Example 1

Three beverages are prepared and are standardized to contain about 8 ppm of dissolved oxygen. The first beverage (beverage 1) is freshly brewed coffee which contains 1% by weight of soluble coffee solids. The second beverage (beverage 2) is prepared from a commercially available instant coffee and contains 1% by weight of soluble coffee solids. The third beverage (beverage 3) is freshly brewed coffee which contains 1% by weight of soluble coffee solids, 0.1% by weight of Novozym® 358 enzyme preparation, 0.1% by weight of glucose, and 0.008% by weight of sodium sulfite. The beverages are held in containers open to the ingress of air and the concentration of dissolved oxygen is determined at regular intervals.

The results are as follows:

| Time (minutes) | Dissolved $O_2$ (ppm) Beverage 1 | Dissolved $O_2$ (ppm) Beverage 2 | Dissolved $O_2$ (ppm) Beverage 3 |
| --- | --- | --- | --- |
| 0 | 8 | 8 | 8 |
| 5 | 4.7 | 7.5 | 2 |
| 10 | 4.3 | 7.0 | 0.4 |
| 15 | 4.1 | 6.6 | 0.5 |
| 20 | 3.9 | 6.4 | 0.5 |
| 25 | 3.6 | 6.1 | 0.5 |
| 30 | 3.4 | 6.0 | 0.5 |
| 35 | 3.3 | 6.0 | 0.5 |
| 40 | 3.2 | 5.9 | 0.5 |
| 45 | 3.1 | 5.9 | 0.5 |
| 50 | 3.0 | 5.9 | 0.5 |
| 55 | 3.0 | 5.9 | 0.5 |
| 60 | 3.0 | 5.9 | 0.5 |

The results indicate the antioxidant system in beverage 3 removes dissolved oxygen much faster than freshly brewed and instant coffee. Therefore the antioxidant system is able to adequately compete with the coffee for oxygen; hence protecting the coffee from oxygen damage.

Example 2

Cans containing coffee solids are prepared. All cans contain about 1% by weight of coffee solids, about 5% by weight of sugar, about 0.065% by weight of sodium bicarbonate, and about 0.01% by weight of lysine. All cans are filled and sealed under the same conditions. During filling, the contents of each can are exposed to air.

Certain of the cans (the "Test cans") also contain an antioxidant system of 0.1% by weight of glucose, 0.01% by weight of Novozym® 358 enzyme preparation, and 0.005% by weight of sodium sulfite The other cans form a control (the "Control cans").

After 1 hour, 1 can from each group is opened and the dissolved oxygen is determined. The remaining cans of each group are then retorted and allowed to cool. After 12 days, a can of each group is opened and a sensory panel is used to analyze the aroma and flavor of the sample.

| Group | Time (hours) | Dissolved $O_2$ (ppm) | Aroma & Flavor |
| --- | --- | --- | --- |
| Test | 1 | 0.9 | Fresh, clean flavors and aroma with roasty notes. Less acidity. |
| Control | 1 | 6.8 | Acid notes present. Prune-like, bland flavor. |

The beverage of the test group has much less dissolved oxygen and much improved flavor and aroma.

Unopened cans of each group are stored for 10 weeks at room temperature and are then opened. The pH is determined. The beverage of the Control cans has a pH of about 5.5 while the beverage of the Test cans has a pH of about 5.7. A sensory panel is used to analyze the aroma and flavor of the beverage of the Test cans and it is found to have fresh, clean flavors and aroma.

Example 3

Roast and ground coffee is placed in an extraction system. The conditions are not oxygen free. The coffee is then extracted with one of three different types of deionized water at a temperature of about 25° C. to 40° C. The first type, Type A, is untreated deionized water. The second type, Type 1, is deionized water which is treated with an antioxidant system of 0.05% by weight of glucose, 0.01% by weight of Novozym® 358 enzyme preparation, and 0.005% by weight of sodium sulfite. The third type, Type 2, is deionized water which is treated with an antioxidant system of 0.05% by weight of glucose, 0.1% by weight of Novozym® 358 enzyme preparation, and 0.005% by weight of sodium sulfite. The dissolved oxygen content of each type of deionized water and each extract is determined.

Each extract obtained is diluted with a sugar solution to provide a coffee beverage containing about 1% by weight of coffee solids. Each beverage is then filled into cans and the cans sealed. A can of each beverage is opened and the dissolved oxygen content of the beverage is determined. The remaining cans are retorted.

| Water Type | $O_2$ Conc (ppm) in Extraction Water | $O_2$ Conc (ppm) in Extract | $O_2$ Conc (ppm) in Beverage |
| --- | --- | --- | --- |
| A | 7.79 | 2.54 | 0.81 |
| 1 | 2.96 | 0.86 | 0.08 |
| 2 | 0.04 | 0.15 | 0.07 |

The results indicate that reducing the oxygen content of the extraction liquid greatly reduces the oxygen content in the resultant beverage, despite the beverage being produced under conditions which are not oxygen free.

Unopened cans of each group are stored for 10 weeks at room temperature and are then opened. A sensory panel is used to analyze the aroma and flavor of the beverages in the cans. The beverages produced using water Types 1 and 2 have a fresh, clean flavor and aroma. The beverages produced using water Type A have an unacceptable flavor and aroma.

We claim:

1. A ready to drink coffee beverage which includes an antioxidant system, the system comprising an inorganic oxygen scavenger and an enzyme composition consisting essentially of glucose oxidase, a glucose oxidase substrate and a catalase.

2. A beverage according to claim 1 which contains about 0.001% to about 0.1% by weight of glucose oxidase.

3. A beverage according to claim 1 which contains about 0.005% to about 0.5% by weight of glucose oxidase substrate.

4. A beverage according to claim 1 in which the inorganic oxygen scavenger is a sulfite.

5. A beverage according to claim 4 which contains about 0.001% to about 0.05% by weight of sulfite.

6. A beverage according to claim 4 in which the sulfite is sodium sulfite.

7. A beverage according to claim 1 which contains less than about 1 ppm of dissolved oxygen.

8. A ready to drink coffee beverage which comprises soluble coffee solids, a sweetener, about 0.001% to about 0.03% by weight of a sulfite, and an enzyme composition consisting essentially of about 0.005% to about 0.1% by weight of glucose oxidase, about 0.01% to about 0.3% by weight of a glucose oxidase substrate and a catalase.

9. A beverage according to claim 8 which is a black coffee beverage.

10. A beverage according to claim 8 in which the sulfite is sodium sulfite.

11. A leverage according to claim 8 which contains less than about 1 ppm of dissolved oxygen.

12. A coffee concentrate which includes an antioxidant system, the system comprising an inorganic oxygen scavenger and an enzyme composition consisting essentially of glucose oxidase, a glucose oxidase substrate, and a catalase.

13. A coffee concentrate according to claim 12 which contains about 0.001% to about 0.1% by weight of glucose oxidase, and about 0.005% to about 0.5% by weight of a glucose oxidase substrate.

14. A coffee concentrate according to claim 12 in which the inorganic oxygen scavenger is a sulfite.

15. A coffee concentrate according to claim 14 which contains about 0.001% to about 0.05% by weight of sulfite.

* * * * *

UNITED STATES PATENT AND TRADEMARK OFFICE
CERTIFICATE OF CORRECTION

PATENT NO. : 6,093,436
DATED : July 25, 2000
INVENTOR(S) : Ying Zheng et al.

It is certified that error appears in the above-identified patent and that said Letters Patent is hereby corrected as shown below:

Column 8,
Line 7, change "leverage" to -- beverage --.

Signed and Sealed this

Twenty-fourth Day of May, 2005

JON W. DUDAS
*Director of the United States Patent and Trademark Office*